United States Patent [19]

Achter et al.

[11] Patent Number: 4,909,089

[45] Date of Patent: Mar. 20, 1990

[54] WALK-IN INSPECTION APPARATUS FOR PRODUCING AIR SAMPLES

[75] Inventors: Eugene K. Achter, Lexington; Edward J. Burke, Waltham; Gabor Miskolczy, Carlisle; Ain A. Sonin, Lexington, all of Mass.

[73] Assignee: Thermedics Inc., Woburn, Mass.

[21] Appl. No.: 272,845

[22] Filed: Nov. 18, 1988

[51] Int. Cl.$^4$ .............................................. G01N 1/14
[52] U.S. Cl. ............................... 73/863.11; 73/863.83
[58] Field of Search .................. 73/23, 863.11, 863.31, 73/863.33, 863.81, 863.83, 863.84, 863.86, 864, 864.81; 340/632, 633, 634

[56] References Cited

U.S. PATENT DOCUMENTS

| | | | |
|---|---|---|---|
| 3,765,842 | 10/1973 | Purt | 340/633 |
| 3,998,101 | 12/1976 | Bradshaw | 73/864 |
| 4,045,997 | 9/1977 | Showalter | 73/23 |
| 4,202,200 | 5/1980 | Ellson | 73/23 |
| 4,718,268 | 1/1988 | Reid et al. | 73/864 |
| 4,736,637 | 4/1988 | Stock | 73/863.83 |
| 4,813,984 | 3/1989 | Griffis | 73/863.31 |

OTHER PUBLICATIONS

Lourence et al., "Flexible Bags Collect Gas Samples", Control Engineering, Sept. 1967, p. 105.
Spangler, G. E. et al., "Analysis of Explosives and Explosive Residues with Ion Mobility Spectrometer (IMS)", Mar. 29–31, 1983, pp. 267–282.

Primary Examiner—Robert R. Raevis
Attorney, Agent, or Firm—Herbert E. Messenger

[57] ABSTRACT

Disclosed is a walk-in inspection apparatus for active production of air samples containing vapors of explosives, drugs, or other substances carried by a person. The apparatus includes a U-shaped booth with an open end through which a person walks past walls which may contain a metal detector, then stands facing a vertical end wall. In the collection of an air sample a blower outside the booth sucks a large volume of air around the person and horizontally through a vertical array of shaped funnels in the end wall and through ducts connected to a collection manifold for subsequent analysis. Infrared heaters in the end wall heat the clothing and skin of the person during sampling, and many small nozzles extending through the end wall direct low volume, high momentum pulsed jets of puffs of air at the person to dislodge vapors, expel air from beneath clothing, and disrupt stagnant boundary layers of air near the person. Curved shapes of portions of the booth and funnels provide smooth, low loss airflow, and height and distance sensors facilitate automatic operation of the inspection apparatus.

23 Claims, 5 Drawing Sheets

WALK-IN INSPECTION APPARATUS FOR PRODUCING AIR SAMPLES

This invention was made with Government support under Contract No. DTR5-57-84-C00063 awarded by the Department of Transportation. The Government has certain rights in this invention.

BACKGROUND OF THE INVENTION

This invention relates to apparatus for inspection of persons and more particularly to a walk-in inspection apparatus for producing air samples containing vapors of selected compounds such as explosives or drugs carried by a person.

Systems are known for acquiring air samples from subjects for detection of substances which emit vapors. For example, U.S. Pat. No. 4,202,200 describes apparatus for detecting explosives including an open-ended tunnel with two opposed pairs of apertures spaced at different distances along the tunnel walls. Air is circulated across the tunnel and through ducts connecting the apertures, and explosives detectors in one or more of the ducts detect vapors of explosives stripped from a person or vehicle positioned in, or passing through, the tunnel.

Systems of the type disclosed in the above-referenced U.S. Pat. No. 4,202,200 offer savings in time and labor when compared to hand-held sensors which are moved over a vehicle or the clothing of a person to be inspected. However, these automatic systems may result in the sampling of a non-representative portion of the air flowing past a subject, or the sampling of air flowed over less that the entire body of a person. Such incomplete sampling presents a risk of failure to detect concealed explosives or other substances. Also, the systems use similar arrangements for both vehicles and persons, and may be perceived as intimidating or quite uninviting places by people being screened. Moreover, diffusion of vapors into the collection air stream may be inadequate to provide samples containing concentrations of substances sufficient for their detection.

An object of the present invention is to provide improved apparatus for producing air samples containing vapors of selected compounds carried by a person.

It is an object of the invention to provide an improved walk-in system for automatically producing air samples from persons for use in screening them for chemical compounds such as explosives, drugs, or other vapor-emitting materials.

It is an object of the invention to provide a walk-in system for rapid, automatic production of air samples and which flows air over, and collects air from, essentially the entire body of a person to be screened for selected vapor-emitting materials.

It is an object of the invention to provide a walk-in system which includes active devices to enhance release of vapors of selected compounds from the clothing and skin of a person.

It is an object of the invention to provide a walk-in air sampling system which minimizes the loss of vapors to walls and other surfaces during collection of air samples.

SUMMARY OF THE INVENTION

The invention is a walk-in inspection apparatus for producing air samples containing vapors of selected compounds carried by a person, particularly materials such as explosives, heroin, cocaine, or others which may be hidden on the person or present as residues on the person's clothing or skin. The apparatus provides air samples from which the vapors may subsequently be detected in a suitable detector. The inspection system of the invention includes a booth, preferably U-shaped with an open end for walk-in entry of a person, and devices for actively producing and collecting an air sample from air flowed in contact with a person standing near an end wall of the booth. Exit of the person from the booth may be either through the open end or through a door in a side wall.

In a preferred embodiment several aerodynamically-shaped funnels are mounted in a vertical array near the center of the booth end wall. The funnels are connected to ducts leading to a collection manifold and a suction blower outside of the booth, and a suitable vapor detector is provided for analysis of the sample. Heaters such as infrared lamps are positioned on either side of the funnel array to heat the clothing and skin of a person standing near the funnels, and thus to raise the vapor pressure of substances to be collected in an air sample. Air jet nozzles are also mounted in the end wall and are operable to direct low volume, relatively high velocity pulsed jets of air towards a person standing in position to be inspected. The jets or air puffs shake the person's clothing, helping to dislodge vapors and to expel air from beneath clothing, and also to scrub the person's skin and break up stagnant boundary layers of air near the person.

In the production of a sample by the inspection apparatus of the invention, a person walks into the booth and stands in position near the funnels. With the suction blower, heat lamps, and air jet nozzles in operation, an air flow field is created, as determined by the curved shape of the closed end of the booth, the funnels, the air flow rate, and the presence of the person in the booth. Vapors stripped from the person, with the active assistance of the air puffs and heat, enter the flow field and are transported in an air sample through the funnels to the collection manifold. Analysis of the air sample produced by the inspection apparatus of the invention reveals the presence or absence of vapors of explosives, drugs, or other substances.

Detailed Description of Preferred Embodiments

The apparatus of the present invention is useful in producing, for subsequent analysis in an appropriate detector, air samples of certain substances which give off vapors and which are carried by persons—i.e., concealed on a person or present on or within the person's clothing. Included among the substances of interest are explosives such as trinitrotoluene (TNT), dinitrotoluene (DNT), pentaerythritol tetranitrate (PETN), nitroglycerin (NG), cyclo 1,3,5-trimethylene-2,4,6-trinitramine (RDX), and ammonium nitrate; drugs such as cocaine and heroin; and chemical warfare agents such as mustard gas and organo-phosphate compounds. For the purpose of this invention and the descriptions contained herein, "vapor" means not only vapors in the gas phase but also aerosols containing the substances of interest in dissolved form, and small mobile particles comprised of the substances themselves or on or within which the substances are trapped.

Figure 1:
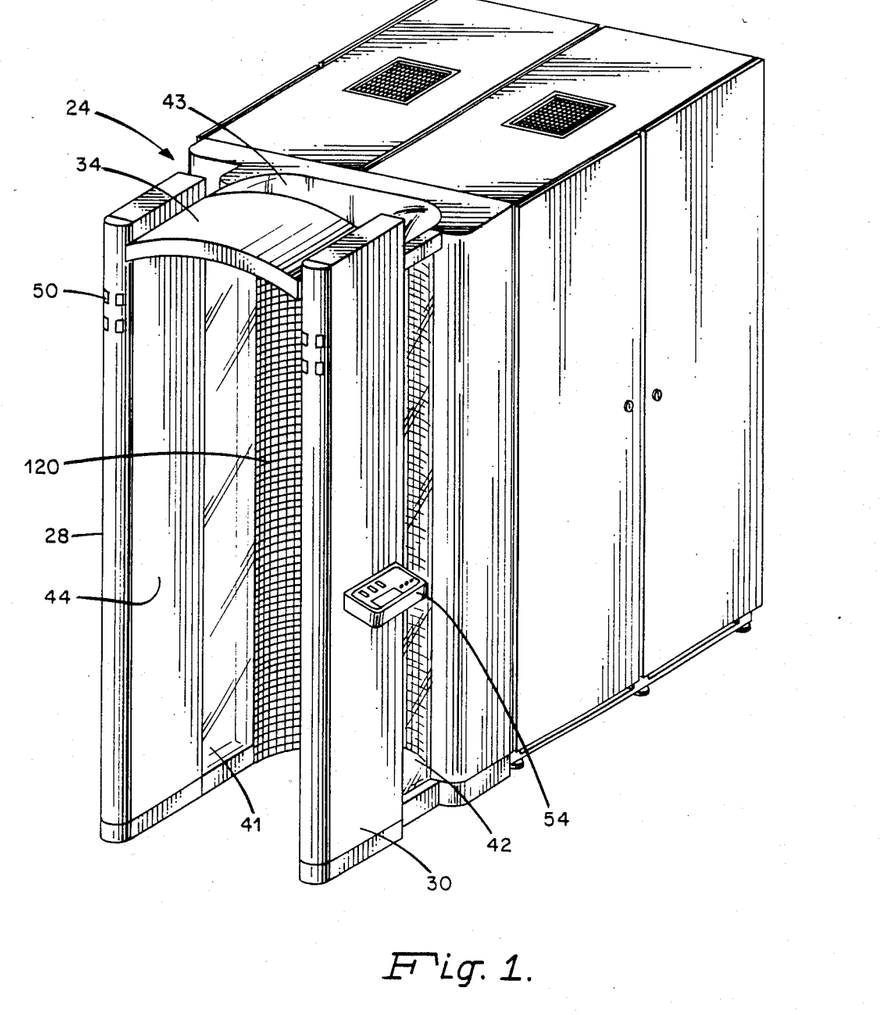
FIG. 1 is a perspective view of the walk-in inspection apparatus of the invention.
Figure 2:
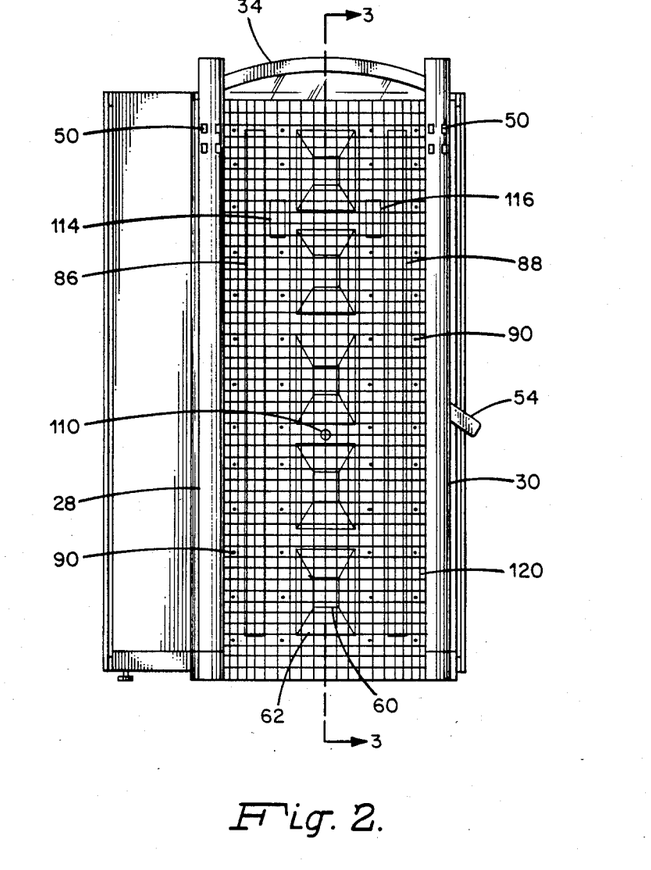
FIG. 2 is a front elevational view of the inspection apparatus of FIG. 1.

A preferred inspection apparatus 20 according to the invention (FIGS. 1-4) includes a walk-in booth 24 formed by two opposed side walls 28 and 30, a top 34, and an end wall 40. Except for the open front end through which a person may enter and leave the booth 24 and for passages formed in the end wall 40 to accommodate equipment described hereinafter, the booth 24 is substantially airtight when installed in an upright position on a floor or other horizontal surface (FIGS. 1 and 2). A typical inspection space defined by the walls and top is about 7 feet high by 2.5 feet wide by 3.75 feet deep.

To minimize feelings of confinement by a person within the booth 24, portions of its side walls 28 and 30 and of the top 34, particularly those near the end wall 40, may be illuminated or, more preferably, are formed of clear plastic or of glass. The clear or translucent portions, designated at sections 41, 42 and 43, also admit light from outside of the booth 24 and allow observation of the person being inspected from either side of the booth 24.

The illuminated or light-transmitting sections 41, 42, and 43 provide a further benefit associated with their contrast with the opaque front portions of the side walls 28, 30 and top 34 of the booth 24. Because the booth 24, when viewed from the front, has the appearance of a tunnel with light near its closed end, a person facing its open end perceives the booth as more inviting to enter than he/she would a uniformly illuminated booth or one whose front portions are lighter than or offer little contrast with, rear portions. As a result the booth "draws" people in or lessens any uneasiness they might feel in entering for inspection.

Although not required for operation of the inspection apparatus in producing air samples from a person, the inspection apparatus 20 illustrated in FIGS. 1-4 includes a metal detector within the opposed panels 44 and 46 forming the front portion of the walk-in booth 24. The metal detector comprises conventional low level electromagnetic devices embedded in either or both panels 44 and 46. Also provided in the front edges of the wall panels 44 and 46 are lights 50 which may be of different colors for indicating whether the booth is unoccupied and available for entry of a person. The lights are electrically connected to an operator control panel 54 mounted on the outside of the side wall 30 and which may be used to display the condition and control the functioning of certain electrically-operable components of the inspection apparatus.

Figure 3:
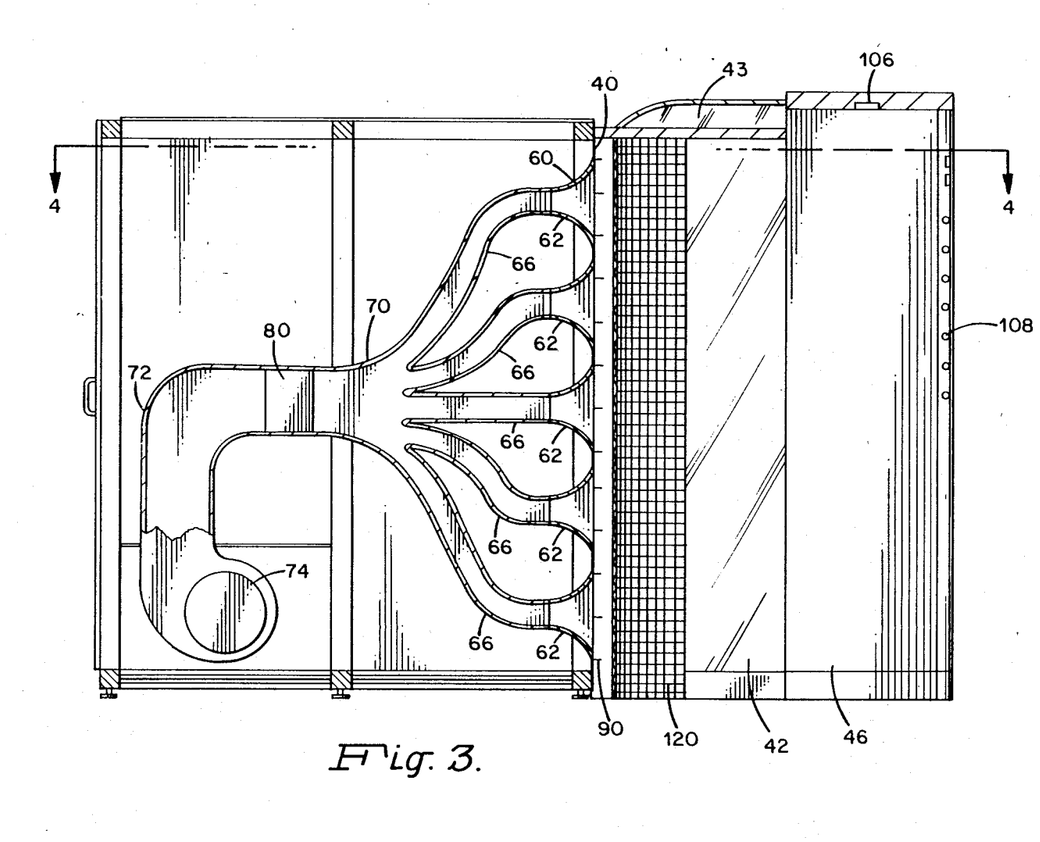
FIG. 3 is a side elevational view of the inspection apparatus taken along line 3—3 of FIG. 2.

As best shown in FIGS. 2 and 3, the end wall 40 of the inspection booth 24 includes a vertical array of equally-spaced apertures 60 in which funnels or aerodynamically-shaped inlets 62 are mounted for withdrawal of air from the booth 24. The funnels 62, five being shown in FIGS. 2 and 3 by way of illustration, extend over the entire height of the inspection space defined by the end wall 40, so as to permit withdrawal of air in a substantially horizontal direction from around each exterior surface of a person standing in the booth 24. Behind the end wall 40 and within an enclosure 64 are collection ducts 66, with each having one end connected to the outlet of a funnel 62, and the opposite end connected to a collection manifold 70. The manifold 70 in turn is connected to a duct 72 leading to a fan or suction blower 74 which is operable to rapidly draw a large volume of air from within the booth 24 through the ducts 66, the collection manifold 70, and the duct 72. A vapor detector, indicated schematically at 80 though not forming part of the present invention, may be contained within, or extend into, the duct 72 between the manifold 70 and the blower 74 to detect specific vapors in the air sample. Although not shown, the duct 72 may contain a valve and side branch to bypass the vapor detector 80 so that the suction blower 74 may operate continuously regardless of whether air samples are being taken and directed into the vapor detector 80.

The instrument employed as the vapor detector 80 may be one of several different types, depending on the specific vapors to be identified in the air sample and the sensitivity and speed of detection required. For example, the vapor detector may be a mass spectometer, as described in U.S. Pat. No. 4,718,268, to Reid et al., which is operable to detect explosives and may also detect chemical warfare compounds. Other suitable instruments are detectors such as a flame ionization detector or a nitric oxide analyzer with a chemiluminescence detector as described in U.S. Pat. No. 4,301,114 to Rounbehler.

Figure 4:
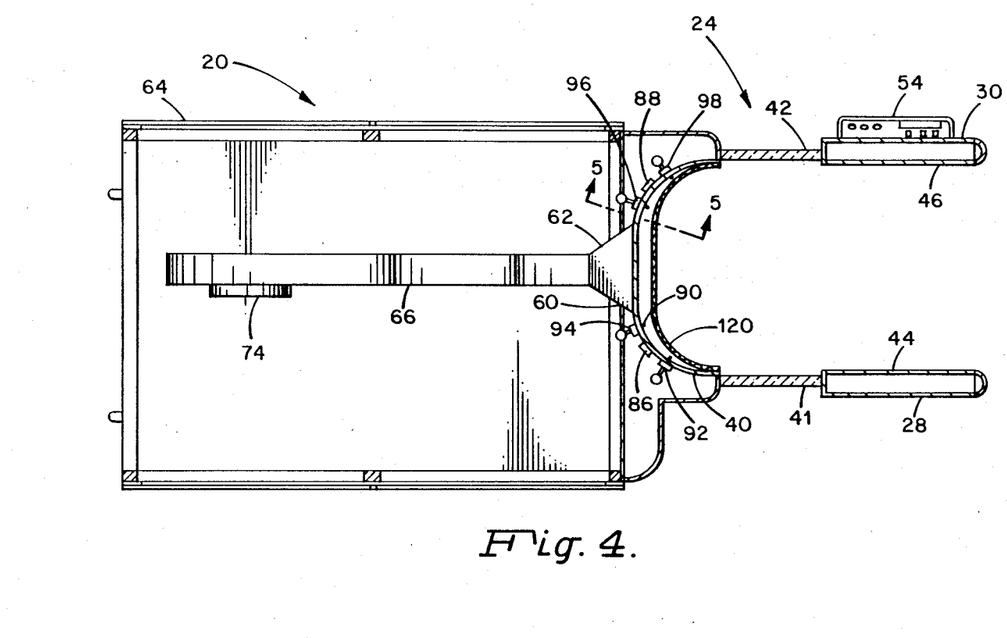
FIG. 4 is a top view of the inspection apparatus taken along line 4—4 of FIG. 3.

Also mounted in the end wall 40 on each side of the funnels 62 are narrow strip heaters 86 and 88 which extend over a substantial portion of the height of the booth 24. The heaters 86 and 88, which preferably include electrically-powered infrared heating elements having little or no visible light output, are operable to heat the clothing and skin of a person standing at a designated position facing the end wall 40, as shown in FIG. 4. Heating raises the vapor pressure of explosives and/or other substances which may be concealed or present in trace quantities on the skin or clothing of the person. This enhances release of the substances into the flow field of air created by the blower 74 sucking an air sample through the funnels 62.

Figure 5:
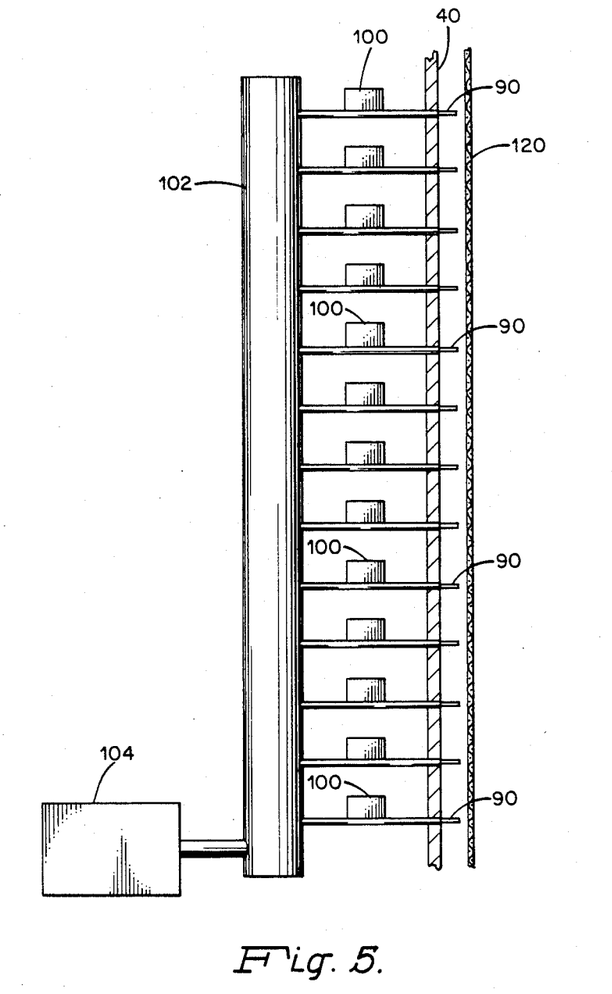
FIG. 5 is an elevational view taken along the line 5—5 of FIG. 3 and illustrating, in enlarged scale from that of FIG. 3, an array of air jet nozzles extending through the end wall of a booth forming part of the inspection apparatus.

As is best shown in FIGS. 2, 4, and in the enlarged elevational view of FIG. 5, arrays of air nozzles 90 also extend through the end wall 40. A preferred arrangement comprises a vertical column of spaced, small diameter nozzles on either side of each of the heaters 86 and 88 for a total of four columns 92, 94, 96, and 98. Each column includes several nozzles (e.g. 13 nozzles of 1/16 inch diameter—see FIG. 5) spaced several inches apart over a substantial portion of the height of the booth so as to direct jets of air at a person standing near the end wall 40. Each nozzle 90 in a column is in communication through a valve 100 with a reservoir of pressurized air such as a vertical pipe 102 which is connected to an air compressor 104 or other source of pressurized air. By rapid opening and closing of the valves 100, which may be solenoid valves operable automatically in a predetermined sequence, the nozzles 90 operate in a pulsed mode to deliver puffs or jets of air at relatively low volume and relatively high momentum. Sequential or staggered operation of the valves (rather than simultaneous operation) is preferred so as to maintain high pressure levels in the reservoir 102. Any or all columns of nozzles may be employed—for example, in certain applications only the outboard columns 92 and 98 are used.

The puffs of air from the nozzles 90 shake the clothing of a person being inspected in the booth 24, thus releasing vapors of explosives and/or other substances, and also help expel air which may contain vapors from beneath the person's clothing. The air puffs also scrub vapors from exposed skin and enhance the effectiveness of air drawn over a person by breaking up or reducing the thickness of the stagnant boundary layer of air directly adjacent the skin and clothing of the person. A suitable series of air puffs for each nozzle 90 of the embodiment of the inspection apparatus shown and described herein is 5 puffs of approximately 0.1 second duration during a sample acquisition about 5 seconds in length.

To avoid discomfort which might arise from the impact of air jets in the face of a person being inspected, at least the upper nozzles 90 of each column 92, 94, 96, and 98 are electrically connected to a height sensor such as a sensor 106 mounted in the top 34 near the open end of the booth 24. Alternatively, each of selected upper nozzles 90 may be connected to one of a vertical array of height sensors 108 mounted in the panels 44 and 46 forming the front portion of the booth 24. These height sensors 108 may, for example, comprise an emitter/collector couple mounted in the panel 44 or 46 with a reflecting element positioned in the opposite panel. As a person walks into the booth 24, the height sensor determines the height of the person and suppresses subsequent operation of one or more nozzles whose air puffs would otherwise be directed into the face of the person.

As best shown in FIG. 4, the end wall 40 of the booth 24 includes curved portions where it joins the side walls 28 and 30. The top may also have a curved section near the end wall 40. The curved walls, and the streamlined shape of the funnels 62 through which air is withdrawn from the booth 24, results in a smooth, even flow of air around a person and into the collection manifold 70 during sampling. This permits large volumes of air and included vapors to be collected rapidly and without large flow losses. It also facilitates collection of air samples drawn over the complete exterior surface of a person so that no areas are missed where substances to be detected may be concealed. Moreover, the smooth flow substantially avoids contact of the air flow drawn from around a person with the walls of the booth. (Such contact would result in sticking and loss of vapors.)

The booth 24 also includes a sensor to determine the distance of a person from the end wall 40. A distance sensor 110 mounted near the center of the end wall 40 may be connected to indicator lights 114 and 116 in the end wall 40 and to audio equipment (not shown) in the booth 24 which instruct a person to walk into the booth for inspection and which also indicate whether the booth is occupied. For example, the indicator 114 may illuminate a walking symbol when the booth 24 is unoccupied and until a person enters and approaches close to a vertical mesh screen 120 near, but spaced from, its end wall 40. In response to a signal from the distance sensor 110, the indicator light 114 may then automatically switch off, the indicator light 116 may illuminate a "booth occupied" symbol, and a sampling sequence may be initiated utilizing air puffs from the nozzles 90, heat from the heaters 86 and 88, and airflow produced by the suction blower 74.

The mesh screen 120 near the end wall 40 prevents a person from contact with the heaters 86, 88, the funnels 62, and the nozzles 90. Preferably the mesh screen 120 is lighter in color than the end wall 40 or the funnels 62 (which may be painted black) so as to preferentially attract the attention of a person facing the screen 120. This contrast lessens any uneasiness or discomfort associated with undue notice of the sampling equipment mentioned within the end wall 40.

During operation of the sampling system 20 a person enters the unoccupied booth 24 by walking into its open end. The person is first screened for the presence of metal objects and, provided no alarm is activated by a metal detector in the panels 44 and 46, approaches the end wall 40 and halts near the mesh screen 120 facing the end wall. A sampling sequence of about 5 seconds duration is automatically initiated in response to a signal from the distance sensor 110, with air passed over the person and withdrawn through the funnels 62 into the collection manifold 70, and on into a suitable vapor detector 80. Active release of vapors from the skin and clothing of the person is promoted by heat from the heaters 86, 88 and air puffs from the nozzles 90 directed to the person. After sampling is complete, visual and/or audio instructions are given for the person to turn and walk out of the booth 24. (If desired, sampling may continue after the person has turned and is facing the open end of the booth). Finally, as the person is turning and walking out of the booth 24, the sample produced by the inspection system 20 may be analyzed in the vapor detector 80 for the presence of vapors of selected substances such as explosives, drugs, or chemical warfare compounds. If the sample is found to contain the target substance, the vapor detector may trigger an alarm in the inspection apparatus so that the person may be reinspected and/or detained and searched manually.

While the invention has been shown and described with reference to preferred embodiments thereof, it is apparent that the walk-in inspection apparatus may be embodied in other specific forms without departing form the spirit or essential characteristics of the invention. For example, although the inspection apparatus is illustrated as capable of collecting all the air flowed over a person to be screened and delivering this large volume of air to a vapor detector, the apparatus may include devices for mixing air withdrawn from the booth and passing only a portion of this homogeneous stream to a vapor detector, dumping the rest; and it may also include devices for trapping and concentrating vapors in the air stream. In addition, although the booth is shown as providing walk-in entry and walk-out exit of a subject through its open end, one or more doors may be included in a side wall so that access, particularly exit, to/from the booth is obtained through the door(s). The scope of the invention is indicated by the appended claims, and all changes which come within the range of equivalency of these claims are intended to be embraced therein.

What is claimed is:

1. Apparatus for producing an air sample containing vapors of selected compounds carried by a person comprising:

a booth sized to permit walk-in entry of a person and walk-out exit therefrom, said booth including a top, a pair of opposed generally vertical side walls, and a generally vertical end wall connected to said side walls and having at least one air passage therethrough;

air jet means for directing jets of air into said booth to contact a person positioned within the booth, said air jet means including a plurality of nozzles mounted in said end wall in position to direct jets of air at the clothing and skin of a person standing at a predetermined location within the booth; and means for withdrawing air and vapors present in said air from within said booth through the air passage in said end wall, said withdrawal means operable, in cooperation with said air jet means, to produce an air sample containing vapors of said selected compounds removed from a person positioned within said booth.

2. Apparatus as in claim 1 wherein said booth has an open end opposite said end wall for walk-in entry of a person.

3. Apparatus as in claim 1 including an air-pervious vertical screen spaced from said end wall of the booth, said screen positioned near the desired location at which a person is to be sampled and preventing the person from contacting said air jet means.

4. Apparatus as in claim 1 including means for pulsing a flow of air through said nozzles to produce puffs of air at relatively low volume and relatively high momentum.

5. Apparatus as in claim 1 wherein said end wall has a vertical array of passages spaced one from another over a substantial portion of the height of the end wall, and said withdrawal means includes a shaped inlet extending through said end wall in each of said passages and operable to receive a substantially horizontal flow of air and vapors from within the booth.

6. Apparatus as in claim 5 wherein said withdrawal means includes a suction blower, a collection manifold in communication with said blower, and a collection duct associated with each of said shaped inlets, said collection ducts each having an inlet end connected to one of said shaped inlets and an outlet end connected to said collection manifold.

7. Apparatus as in claim 5 including first and second vertical strip heaters extending through said end wall and positioned, respectively, on opposite sides of said vertical array of passages.

8. Apparatus as in claim 6 wherein said air jet means comprises first and second vertical columns of nozzles extending through said end wall and positioned, respectively, on opposite sides of said vertical array of passages, and means for producing a pulsed flow of air through each of said nozzles.

9. Apparatus as in claim 1 including a heater for directing heat into said booth to heat a person positioned within the booth.

10. Apparatus as in claim 1 including means in said side walls for detecting metal objects carried by a person.

11. Apparatus as in claim 1 wherein said booth has an open end opposite said end wall and wherein the portions of said end wall connected to said side walls are curved to facilitate the smooth flow of air and vapors during withdrawal of air and vapors from said booth.

12. Apparatus for producing an air sample containing vapors of selected compounds carried by a person comprising:
a booth sized to permit walk-in entry of a person and walk-out exit therefrom, said booth including a top, a pair of opposed generally vertical side walls, and a generally vertical end wall connected to said side walls and having at least one air passage therethrough;

air jet means for directing jets of air into said booth to contact a person positioned within the booth, said air jet means including a plurality of nozzles mounted in said end wall in position to direct jets of air at the clothing and skin of a person standing at a predetermined location within the booth;

means for withdrawing air and vapors present in said air from within said booth through the air passage in said end wall, said withdrawal means operable, in cooperation with said air jet means, to product an air sample containing vapors of said selected compounds removed from a person positioned within said booth;

a height sensor mounted in said booth; and means for preventing airflow through one or more of said nozzles in response to a signal from said height sensor indicative of the height of a person within the booth.

13. Apparatus for producing an air sample containing vapors of selected compounds carried by a person comprising:
a booth sized to permit walk-in entry of a person and walk-out exit therefrom, said booth including a top, a pair of opposed generally vertical side walls, and a generally vertical end wall connected to said side walls and having at least one air passage therethrough;

air jet means for directing jets of air into said booth to contact a person positioned within the booth, said air jet means including a plurality of nozzles mounted in said end wall in position to direct jets of air at the clothing and skin of a person standing at a predetermined location within the booth;

means for withdrawing air and vapors present in said air from within said booth through the air passage in said end wall, said withdrawal means operable, in cooperation with said air jet means, to produce an air sample containing vapors of said selected compound removed from a person positioned within said booth; and means for pulsing a flow of air through said nozzles to produce puffs of air at relatively low volume and relatively high momentum, said means for pulsing including a reservoir, means for supplying air at high pressure to said reservoir, a valve associated with each said nozzles, and valves connected between said reservoir and said nozzles, and means for rapidly opening and closing said valves in a predetermined sequence to generate puffs of air from said nozzles.

14. Apparatus for producing an air sample containing vapors of selected compounds carried by a person comprising;
a booth sized to permit walk-in entry of a person and walk-out exit therefrom, said booth including a top, a pair of opposed generally vertical side walls, and a generally vertical end wall connected to said side walls and having at least one air passage therethrough;

air jet means for directing jets of air into said booth to contact a person positioned within the booth;

means for withdrawing air and vapors present in said air from within said booth through the air passage in said end wall, said withdrawal means operable, in cooperation with said air jet means, to produce an air sample containing vapors of said selected compounds removed from a person positioned within said booth; and a distance sensor in said booth for determining the distance of a person from said end wall, said distance sensor operable to product signals for controlling the operation of a heater and said air jet means.

15. Inspection apparatus for generating an air sample containing vapors of substances carried by a person, such as vapors of explosives, cocaine, or heroin, comprising:
- a booth including a generally U-shaped vertical wall having two parallel opposed side wall portions and a curved end wall portion connecting the side portions, a top connected to said wall, and an open end opposite said end wall portion;
- a plurality of funnels mounted in a vertical column in said end wall portion and extending over substantially the entire height of said booth;
- a plurality of air jet nozzles mounted in said end wall portion, said nozzles arranged in vertical columns on both sides of said funnels;
- means for pulsing a flow of pressurized air through said nozzles to form puffs of air for contacting the clothing and exposed skin of a person standing near said end wall portion of the booth; and
- means for withdrawing air and vapors present in said air from within said booth through said funnels so as to produce an air sample containing said vapors.

16. Inspection apparatus as in claim 15 including a pair of vertical strip heaters mounted in said end wall portion on opposite sides, respectively, of said vertical column of funnels and operable to heat a person standing near said end wall portion.

17. Inspection apparatus as in claim 15 including a vertical open-mesh screen positioned near said end wall portion.

18. Inspection apparatus as in claim 15 wherein said means for withdrawing air and vapors through said funnels includes, outside of said booth, a collection manifold, a collection duct associated with each of said funnels and connected between a funnel and said collection manifold, and a blower for sucking air and vapors through said collection manifold, said collection ducts, and said funnels.

19. Inspection apparatus as in claim 15 wherein said means for pulsing air comprises an air supply manifold for each column of nozzles, means for supplying air at high pressure to said air supply manifold, a valve connected between said air supply manifold and each of said nozzles, and means for rapidly opening and closing said valves in a predetermined sequence.

20. Inspection apparatus as in claim 19 including a height sensor in said booth for measuring the height of a person entering the booth, and means for causing selected of said valves to remain closed during sampling based on a height measured by said height sensor.

21. Inspection apparatus for generating an air sample containing vapors of substances carried by a person, such as vapors of explosives, cocaine, or heroin, comprising;
- a booth including a generally U-shaped vertical wall having two parallel opposed side wall portions and a curved end wall portion connecting the side portions, a top connected to said wall, and an open end opposite said end wall portion;
- a plurality of funnels mounted in a vertical column in said end wall portion and extending over substantially the entire height of said booth;
- means for withdrawing air, and vapors present in said air, from within the booth through said funnels to generate an air sample containing said vapors, said withdrawal mean operable to create a generally horizontal flow of air and vapors through said booth; and
- means for directing heat into said booth to heat a person standing within the booth.

22. Apparatus as in claim 21 including a distance sensor in said booth for determining the distance of a person from said end wall portion, said distance sensor operable to produce signals for controlling the operation of said heater and said withdrawal means.

23. Apparatus as in claim 21 wherein said means for directing heat into said booth includes first and second vertical strip heaters extending through said end wall portion and positioned, respectively, on opposite sides of said vertical column of funnels.

* * * * *